United States Patent [19]
Bennett

[11] Patent Number: 4,838,881
[45] Date of Patent: Jun. 13, 1989

[54] MULTILUMEN CATHETER AND ASSOCIATED IV TUBING

[75] Inventor: Laurence M. Bennett, Sandy, Utah

[73] Assignee: Deseret Medical, Inc., Franklin Lakes, N.J.

[21] Appl. No.: 250,871

[22] Filed: Sep. 29, 1988

Related U.S. Application Data

[63] Continuation of Ser. No. 607,330, May 4, 1984, abandoned.

[51] Int. Cl.$^4$ .............................................. A61M 25/00
[52] U.S. Cl. ................................. 604/280; 604/283; 156/73.2; 156/294
[58] Field of Search ........................... 604/280, 43–45, 604/283, 269, 273, 284; 156/73.2, 294; 29/528, 507; 264/23, 249, 266; 128/348.1

[56] References Cited

U.S. PATENT DOCUMENTS

| | | | |
|---|---|---|---|
| 399,985 | 3/1889 | Goodwillie . | |
| 1,696,018 | 12/1928 | Schellberg | 604/43 |
| 2,173,527 | 9/1939 | Agayoff | 604/96 |
| 2,561,569 | 7/1951 | Flynn | 18/13 |
| 3,064,653 | 11/1962 | Coanda | 604/280 |
| 3,174,890 | 3/1965 | Goyke | 156/272 |
| 3,322,590 | 5/1967 | Clark | 156/273 |
| 3,467,180 | 9/1969 | Pensotti | 29/523 |
| 3,469,579 | 9/1969 | Hubert . | |
| 3,625,793 | 12/1971 | Sheridan | 156/294 |
| 3,720,210 | 3/1973 | Diettrich . | |
| 3,817,389 | 6/1974 | Weichselbaum | 210/448 |
| 3,976,529 | 8/1976 | Weichselbaum | 156/272 |
| 4,003,665 | 1/1977 | Dreyer et al. | 264/249 |
| 4,050,667 | 9/1977 | Kossett | 249/82 |
| 4,063,980 | 12/1977 | Trunnell | 264/249 |
| 4,072,146 | 2/1978 | Howes | 128/2.05 D |
| 4,072,153 | 2/1978 | Swartz . | |
| 4,178,936 | 12/1979 | Newcomb | 604/43 |
| 4,198,984 | 4/1980 | Taylor | 604/280 |
| 4,210,479 | 7/1980 | Fabisiewicz | 156/273 |
| 4,214,593 | 7/1980 | Imbruce et al. | 128/748 |
| 4,248,224 | 2/1981 | Jones . | |
| 4,268,338 | 5/1981 | Peterson | 156/251 |
| 4,309,994 | 1/1982 | Grunwald . | |
| 4,354,495 | 10/1982 | Bodicky . | |
| 4,364,394 | 12/1982 | Wilkinson | 604/96 |
| 4,384,186 | 5/1983 | Burt | 219/10.81 |
| 4,398,910 | 8/1983 | Blake et al. | 604/93 |
| 4,403,983 | 9/1983 | Edelman et al. | 604/43 |
| 4,405,313 | 9/1983 | Sisley et al. | 604/43 |
| 4,406,656 | 9/1983 | Hattler et al. | 604/280 |
| 4,419,095 | 12/1983 | Nebergall et al. | 604/96 |
| 4,425,177 | 1/1984 | Shinno | 264/249 |
| 4,484,585 | 11/1984 | Baier | 604/280 |
| 4,496,353 | 1/1985 | Overland et al. | 604/280 |

OTHER PUBLICATIONS

"Angulated Soft Rubber Suprapubic Drains", A.C.M.I. Latex.

*Primary Examiner*—Stephen C. Pellegrino
*Attorney, Agent, or Firm*—Aaron Passman

[57] ABSTRACT

A multilumen catheter comprises separate proximal IV tubes of substantially circular cross-section welded in fluid communication with each of the substantially eliptical-shaped lumens of the catheter. The weld, at the interface between the outer surface of each IV tube and the associated lumen sidewall, is continuous over the interface to provide for an integral fluid sealing connection between the catheter lumen and the IV tube.

4 Claims, 3 Drawing Sheets

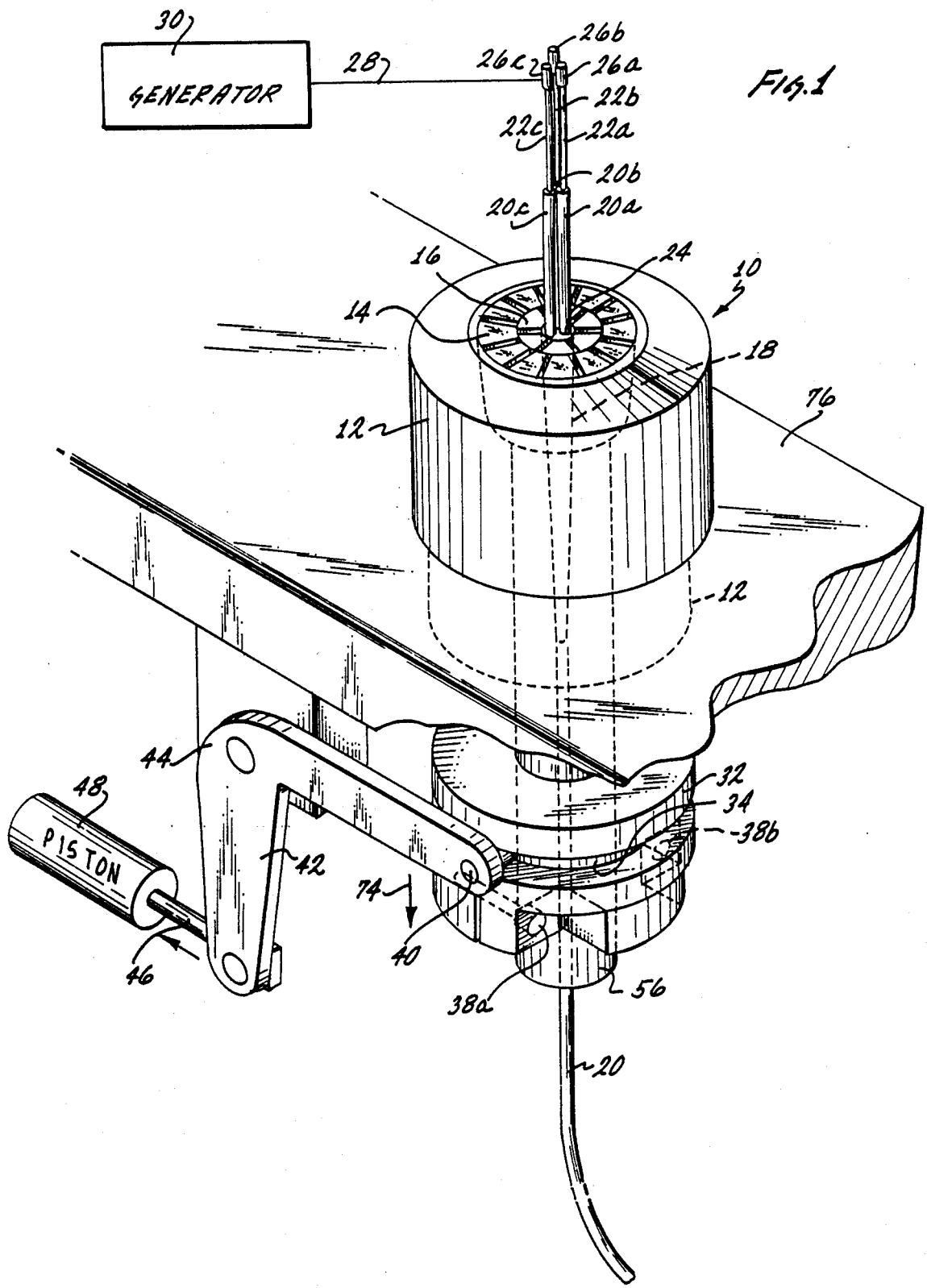

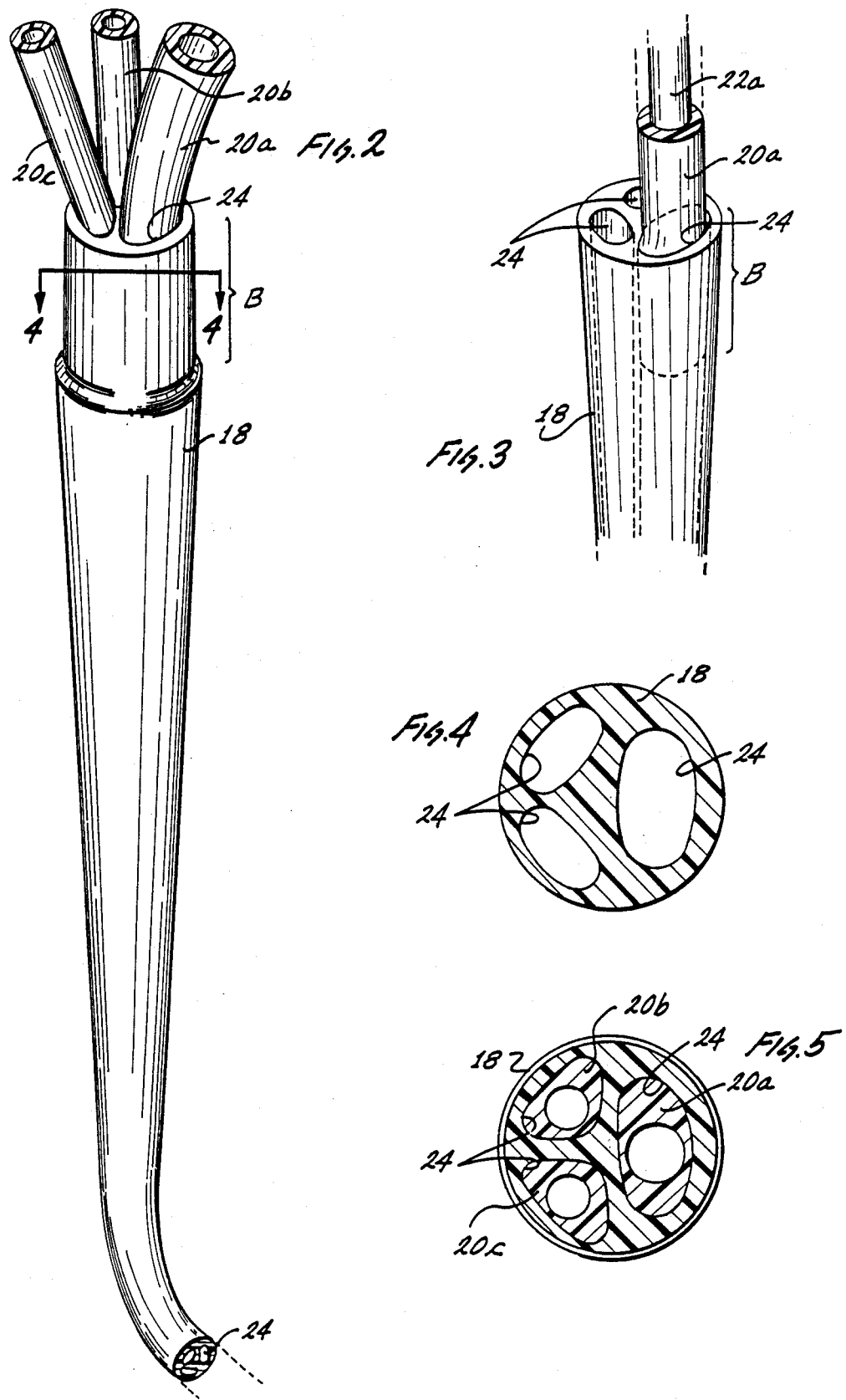

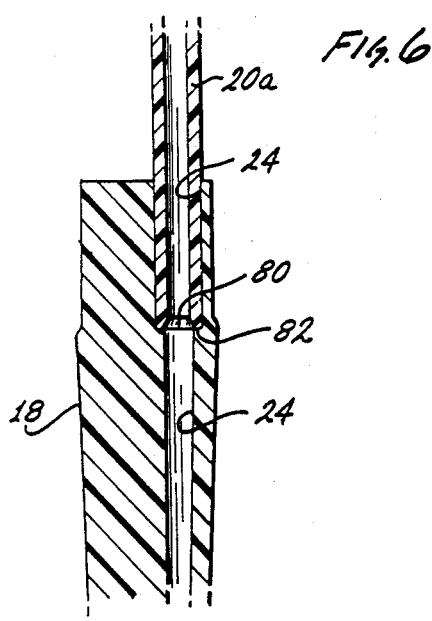
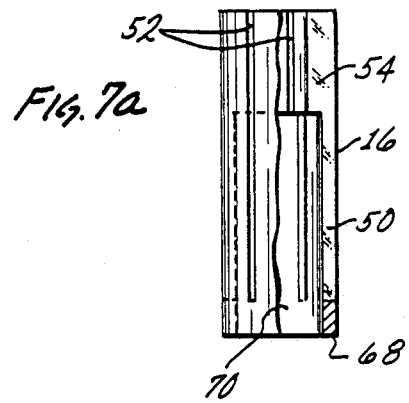
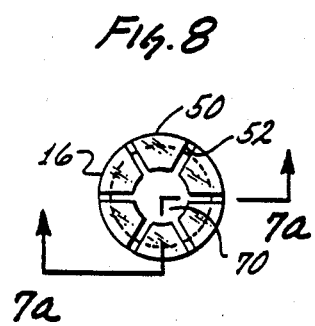
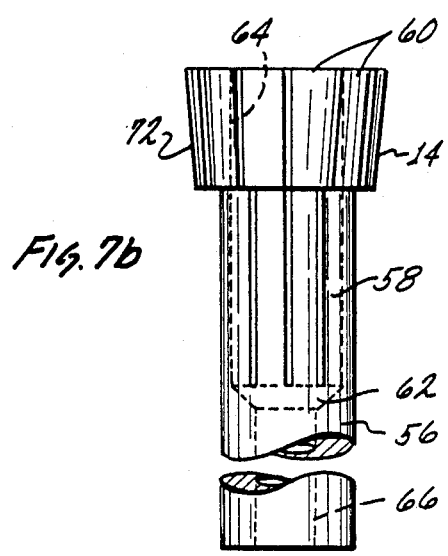
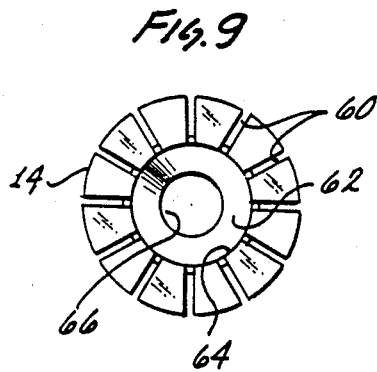
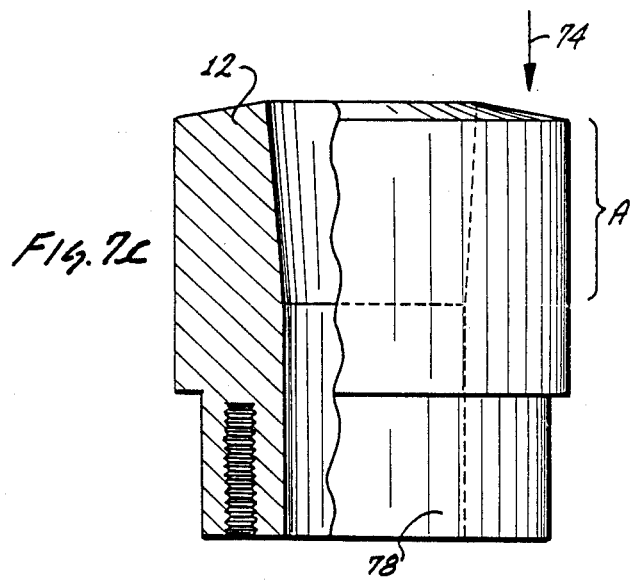

MULTILUMEN CATHETER AND ASSOCIATED IV TUBING

This application is a continuation of application Ser. No. 607,330, filed May 4, 1984, now abandoned.

BACKGROUND OF THE INVENTION

The present invention relates generally to multilumen catheters. More particularly, the present invention relates to multilumen catheters having proximal IV tubes welded directly with the walls of the catheter's lumens to create a continuous and integral bond therebetween. This invention is particularly, though not exclusively, useful as a multilumen catheter having relatively thick walled IV tubes of generally circular cross-section welded to the catheter lumens of generally noncircular cross-section.

DESCRIPTION OF THE PRIOR ART

Numerous health care situations are not uncommon wherein it is necessary to simultaneously give several different medications to the patient. In cases where the various medications can be given as solutions, it is often desirable to intravenously infuse them into the patient through a single puncture site with the use of a multilumen catheter. Indeed, the concept of using multilumen catheters for various medical purposes is well known in the pertinent art. For example, U.S. Pat. No. 4,405,313 to Sisley et al. discloses a dual lumen catheter suitable for surgical implantation. Other U.S. patents which include U.S. Pat. Nos. 550,238 to Allen, 3,394,705 to Abramson, 3,046,988 to Moreau et al., 3,448,739 to Stark et al., 3,746,003 to Blake et al., and 3,805,794 to Schlesinger each disclose multilumen or multi passageway devices for use in the medical arts. Additionally, U.S. Pat. Nos. 4,072,146 to Howes and 4,406,656 to Hattler et al. disclose multilumen venous catheters which teach or suggest use of an adapter for connecting proximal IV tubes to the lumens of multilumen catheters.

Further, the use of an electronic welding current to join plastic parts is known in the art. Specifically, U.S. Pat. No. 3,322,590 to Clark discloses an electronic welding process for making a sealed connection between a tube and a container. Further, U.S. Pat. No. 4,210,479 to Fabisiewicz discloses a method for using RF energy to band a plastic tube to a metal needle and U.S. Pat. No. 4,268,338 discloses use of RF current to seal thermoplastic layers. In U.S. Pat. No. 4,419,095 to Nebergall et al. a method for RF welding a cannula with a radiopague tip is disclosed wherein the inner and outer diameters of the mated elements are uniform so as to not produce projecting edges or ridges at the joint. In none of the cited references, however, is there any teaching of a connection or method for connecting proximal IV tubes with catheter lumens by RF welding to form a continuous and integral bond at the interface between the tube and the lumen.

A common problem with multilumen catheters is their size. In order to minimize trauma to the patient, it is desirable to have the smallest possible puncture. Consequently, a catheter should have the smallest possible cross-sectional area. At odds with this desire is the fact that the flow characteristics of medical solutions within a generally round lumen of a catheter improves with an increase in lumen cross-sectional area in accordance with Poiseuille's Law:

$$F = \frac{\Delta P \pi R^4}{8L}$$

where:
F=Flow
P=Pressure
R=Radius, and
L=Tube Length.

From Poiseuille's Law, it can be appreciated that flow characteristics vary proportionally with the square of the lumen's cross-sectional area. Thus, even moderate increases in lumen cross-sectional area can have a marked effect on flow characteristics. Accordingly, given a catheter having a generally circular cross-section, the shape of the individual lumens within the catheter is an important consideration for optimizing flow characteristics through the catheter.

It can be shown mathematically and empirically that lumens of circular cross-section do not optimize use of the available area in the cross section of a circular catheter. Instead, semi-circular or wedge shaped lumens appear to optimize such use. However, with semi-circular or wedge shaped lumens, the junctures between the surfaces that form the lumens create dead spaces and stagnation areas in the fluid flow. Eliptically shaped lumens, on the other hand, essentially eliminate flow problems caused by lumen wall junctures while at the same time using available catheter cross-section area more efficiently than circular-shaped lumens. Whereas a case can be made that eliptically shaped lumens are optimal for the design of a multilumen catheter, the preferred cross-section for an IV tube remains circular. Thus, for many applications it is necessary and desirable to join an IV tube of generally circular cross-section with catheter lumens which are generally of noncircular cross section.

Various methods for attaching IV tubes to catheters have been proposed in the prior art. For example, one method employs a thermoplastic adapter which is glued into place as a connector between the flared end of the catheter and the proximal IV tubes. Another presently used method requires the glueing of a metal tube into fluid communication between the catheter lumens and the lumen of the IV tube. The joint so formed is then encased in glue and surrounded by a thermoplastic sleeve. Still another method for attaching IV tubes to a catheter uses an insert molded connector for positioning and mating the fluid passageways of a catheter and an IV tube. In each of the above described methods, the connection requires at least one additional part and may even use dissimilar materials. Furthermore, these methods either require expensive injection molding equipment or use glue which can develop leaks and inconsistent pull strengths between the IV tube and the catheter.

Although RF welding has been used in certain operations to weld plastic parts together, the RF welding of IV tubes to the lumens of a catheter poses several heretofore unsolved problems. First, it should be appreciated that RF welding is most effective where there is contact between the surfaces. Consequently, unless the lumen sidewall and the outer surface of the IV tube are placed into contact with each other, gaps and voids are created at the weld. To partially overcome this problem, thin walled IV tubes could be used with increased RF welding energy levels. The molten plastic tube created with this combination may tend to fill in the gaps and voids. Generally, however, thin walled IV tubes have certain disadvantages which make them less attractive for hospital use than the thicker walled tubes. For instance, thin walled tubes kink more easily than thicker walled tubes and are not as capable of developing the increased pull strength or withstanding the higher fluid pressures attainable with thicker tubes.

Accordingly, it is an object of the present invention to provide a means for attaching an IV tube to a catheter which eliminates gaps and voids between the IV tube and catheter at the point of attachment. It is another object of the present invention to manufacture a multilumen catheter which has structural integrity at the juncture of the IV tubes with the lumens of the catheter to achieve increased pull strength between the IV tubes and the catheter. Yet another object is to provide a means for uniformly attaching a plurality of lumens to the respective lumens of a catheter at the same area of the catheter without the need for stretching or pulling the catheter. It is still another object of this invention to provide an integral attachment between relatively thick IV tubes and catheter lumens having incompatible shapes. Another object is to provide a means for insuring uniform engagement of the outer surface of the IV tube with the lumen sidewall to allow use of a lower and more controllable RF energy level that results in increased tool life and that permits use of thicker walled IV tubes.

SUMMARY OF THE INVENTION

The preferred embodiment of the present invention includes a device of unitary construction comprising a multilumen venous catheter having eliptically shaped lumens. Integrally attached to each lumen of the catheter is a proximal IV tube having a generally circular cross-section. In the preferred embodiment the attachments between IV tube and catheter are made in a manner to provide a continuous integral weld therebetween.

The novel features of this invention, as well as the invention itself, both as to its organization and operation will be best understood from the accompanying drawings, taken in conjunction with the accompanying description, in which similar reference characters refer to similar parts, and in which:

BRIEF DESCRIPTION OF THE DRAWINGS

FIG. 1 is a perspective view of an RF welding device having portions broken away and in phantom for illustration and clarification and shown with a mandrel and IV tube in position for the operation of welding the IV tube to the lumen of a catheter;

FIG. 2 is a perspective view of the multilumen catheter and associated IV tubing of the present invention;

FIG. 3 is a perspective view of the multilumen catheter showing an IV tube and mandrel in position for the welding of the IV tube to the catheter;

FIG. 4 is a cross-sectional view of the catheter prior to attachment of the IV tubes as seen along the line 4—4 in FIG. 2;

FIG. 5 is a cross-sectional view of the catheter after attachment of the IV tubes as seen along the line 4—4 in FIG. 2;

FIG. 6 is a cross-sectional view of the area of attachment between the IV tube and the catheter;

FIG. 7a is a side view of a dielectric collet along the line 7a–7a of FIG. 8;

FIG. 7b is a side view of a metal collet with portions shown in phantom for illustration and clarification;

FIG. 7c is a side view of a metal adapter with portions shown in phantom for illustration and clarification;

FIG. 8 is a top view of a dielectric collet of an RF welding device used in the manufacture of the present invention; and FIG. 9 is a top view of a metal collet of an RF welding device used in the manufacture of the present invention.

DESCRIPTION OF THE PREFERRED EMBODIMENT

Referring now to the drawings and particularly to FIG. 1, there is shown a welding device generally indicated by the numeral 10. As seen in FIG. 1 a metal adapter 12 is mounted on a support 76. Operatively associated with metal adapter 12 is a metal collet 14 and a dielectric collet 16 which are operatively associated with each other to clampingly engage and hold the catheter 18 within dielectric collet 16. The interrelation of metal adapter 12, metal collet 14 and dielectric collet 16 can best be appreciated by reference to FIGS. 7a, 7b and 7c, which, taken together, show an exploded arrangement of these elements of the present invention. As can be appreciated by cross reference between FIGS. 1, 7a, 7b and 7c, the dielectric collet 16 nests within metal collet 14, and both are operatively associated with the metal adapter 12 in a manner to be subsequently discussed in greater detail.

Still referring to FIG. 1, it is seen that a collar 32 having a peripheral groove 34 is attached to extension 56 of metal collet 14. A semi-circular shaped band 36 is connected with collar 32 by a screw 38a and a second screw 38b which are generally parallel to each other. Screw 38a and 38b are tightened in a manner that grips extension 56 of metal collet 14 between collar 32 and band 36 to prevent relative motion between collar 32 and extension 56. A pivot arm 42 is rotatably mounted on support 76 by a hinge pin 44. Actuator arm 46 is rigidly attached to pivot arm 42 and operatively coupled to piston 48 to rotate pivot arm 42 around hinge pin 44 in accordance with movement of piston 48. A pin 40 is mounted on pivot arm 42 and is slidably received within the slot 34 of collar 32 to raise and lower metal collet 14 along a line generally indicated by directional arrow 74.

Referring now to FIG. 8 and FIG. 7a, it can be seen that dielectric collet 16 comprises a plurality of resilient members 50 which are separated from each other by the slots 52 and which are integrally attached one with each other at the bottom 68 of dielectric collet 16. Each resilient member 50 further comprises an end portion 54 which is dimensioned and adapted to cooperate with the other resilient members 50 of dielectric collet 16 to clampingly engage catheter 18. Dielectric collet 16 is also formed with a pathway 70 so that as the end portions 54 of resilient member 50 grasp a certain part of the catheter 18, the remainder of catheter 18 can extend on through pathway 70. Preferably, dielectric collet 16 is made of a material known in the relevant art as acetal. It should be appreciated, however, that any dielectric material having sufficient strength and resilience to clampingly engage the catheter 18 is sufficient for the purposes of the present invention.

FIG. 9 and FIG. 7b respectively show a top view and a side view of the metal collet 14. As can be perhaps best seen in FIG. 7b, metal collet 14 comprises a plurality of resilient fingers 58 which are separated from each other by the slots 60 and are integrally joined to the extension portion 56 of metal collet 14 in a manner that permits the cooperation of resilient fingers to clampingly engage upon an object. In FIG. 7b it can also be seen that each of the resilient fingers 58 is formed with a flange portion 72 which extends outwardly from resilient fingers 58 and is tapered or flared for a purpose to be subsequently discussed. Formed throughout the longitudinal length of metal collet 14 is a passageway 64 in the region where the resilient fingers 58 are located and a passageway 66 in the region associated with extension 56. Passageway 64 and passageway 66 are dimensioned so that the diameter of the passageway 64 is greater than the diameter of passageway 66. As best seen in FIG. 7b, this change in dimension of passageway 64 creates a base 62 within the metal collet 14. As can be appreciated by reference to FIGS. 1, 7a and 7b, the dielectric collet 16 is dimensioned to nest within the passageway 64 of metal collet 14 with bottom 68 of dielectric collet 16 resting against base 62 of the metal collet 14. In this configuration the top portion of dielectric collet 16 is flush with the top of metal collet 14. It should now be appreciated that a circumferencial force acting upon metal collet 14 will cause resilient fingers 58 to merge and reduce the diameter of passageway 64 in the region where resilient fingers 58 are located. Consequently, metal collet 14 engages resilient members 50 of dielectric collet 16 in a manner that causes resilient members 50 to merge and reduce the diameter of pathway 70 in the area where end portions 54 of dielectric collet 16 are located.

A metal adapter 12, as shown in FIG. 7c, is formed with a bore 78 having a tapered region generally designated A in FIG. 7c. Considering FIG. 7a, b and c together, it can be appreciated that dielectric collet 16 and metal collet 14 are cooperatively positioned as previously discussed and that the combination of dielectric collet 16 and metal collet 14 are dimensioned to be received into the bore 78 of adapter 12. As the metal collet 14 is positioned within bore 78 of adapter 12, it should be appreciated that the tapered portion of the flanges 72 on metal collet 14 engage with tapered region A of the adapter 12. Thus, a movement of the metal collet 14 in the direction indicated by directional arrow 74 in FIG. 7c will increasingly urge tapered region A against flanges 72 to cause a merging of the resilient fingers 58 on metal collet 14. As previously discussed there will be a corresponding merging of the resilient members 50 of dielectric collet 16. It should be further noted that the length of extension 56 of the metal collet 14 is such that it extends through the bore 78 so as to be exposed for operative engagement with the collar 32 as previously discussed and shown in FIG. 1.

In the preferred embodiment of device 10, adapter 12 and metal collet 14 are made of a beryllium copper alloy. However, adapter 12 may also be made of cold rolled steel and the metal collet 14 may be made of a heat treated spring steel. In either case, or with another material, it is important that metal collet 16 and adapter 12 provide an electrical ground and that metal collet 14 be of sufficient strength and resilience to perform the function of clampingly engaging an object, such as dielectric collet 16, when the object is placed in passageway 64 of the metal collet 14. Further, it can be appreciated by 27 one skilled in the pertinent art that the materials for adapter 12 and metal collet 14 be of sufficient strength to resist continued operation in a manufacturing environment.

FIG. 4 shows a typical cross section of a multilumen catheter 18 having eliptical shaped lumens 24 before the catheter 18 is attached in fluid communication with an IV tube 20a. FIG. 3 shows the association of an IV tube 20a with a lumen 24 of catheter 18 during the welding procedure. As can be better seen with reference to FIG. 3 in preparation for the welding procedure, a mandrel 22a is inserted into the passageway of IV tube 20a. The combination of IV tube 20a and mandrel 22a is then inserted into a lumen 24 of catheter 18. Likewise, mandrels 22b and c are respectively inserted into IV tubes 20b and c and separately inserted into lumens 24 of catheter 18. Although only IV tubes 20a, b and c are discussed here, it must be appreciated that more or fewer IV tubes 20 can be used depending only on the number of lumens 24. For device 10 the mandrels 22a, b and c are made of a beryllium copper alloy. Spring steel, sometimes commonly referred to by those skilled in the art as "piano wire" may, however, also be used for mandrels 22a, b and c. Once the association between IV tubes 20a, b and c and the lumens 24 of catheter 18 has been accomplished, the device 10 can be operated to urge end portions 54 of dielectric collet 16 against catheter 18 to further compressingly engage IV tubes 20a, b and c with lumens 24 of catheter 18. A generator 30 may be of any suitable construction well known in the art which is designed to produce high frequency power for welding plastics and other materials. In the welding operation, generator 30 is connected through a line 28 to connector 26a in a manner well known in the art. The generator 30 is then activated to provide RF energy to the mandrel 22a for welding and reforming the IV tube 20a to the side wall inner surface of a respective lumen 24 in the catheter 18.

Although any commonly used material is acceptable, welding device 10 is particularly useful for work with IV tubes 20a, b or c and catheters 18 which are made of polyurethane. A barium-filled polyurethane to provide the radio pacity characteristic of many preferred catheters is acceptable for use with the welding device 10.

It should be appreciated by one skilled in the art that the metal collet 14 can be eliminated from the welding device 10 without affecting the utility or operation of the welding device 10. In an alternate embodiment, the dielectric collet 16 is formed to function like metal collet 14 of the preferred embodiment and made operable in direct association with the adapter 12 to clampingly engage the catheter 18. With this in mind, it should be understood that metal collet 14 is included in the preferred embodiment for the purpose of providing a more rugged device which is capable of withstanding the repetitive operations likely to be encountered in a manufacturing process. The necessity for metal collet 14 is, in part, caused by material limitations. In particular, the acetal material preferably used in the manufacture of dielectric collet 16 is not suited for the repetitive and continuous operation envisioned in the manufacturing process. Dielectric collet 16, however, when nested in passageway 64 of metal collet 14 is not subjected to the stresses and loads which would cause it to wear out early. Regardless, the utility of welding device 10 is dependant upon an electrical connection wherein the IV tube 20a and the catheter 18, in combination with a dielectric, separate mandrel 22 from an electrical ground. According to the present invention, metal collet 14 and adapter 12 provide the ground. As easily understood by those skilled in the pertinent art, any ground will do. Thus metal adapter 12 alone, as described for an alternate embodiment, will suffice and metal collet 14 could, in fact, be eliminated.

To more fully understand and appreciate the structure of catheter 18 and the attachment of IV tubes 20a, b and c thereto, collective reference is made to FIGS. 2, 3, 4, 5 and 6. FIG. 4 shows a typical cross section of catheter 18 having eliptical shaped lumens 24. On the other hand, IV tubes 20a, b and c typically have generally circular cross-sections. Thus, IV tubes 20a, b and c are incompatible for a directly conforming fit with the eliptical cross-section of lumens 24. Nevertheless, the compressive action of dielectric collet 16 and the subsequent reforming and welding operation mentioned above create a bonded conformity between the outside surfaces of IV tubes 20a, b and c and the respective lumens 24. As seen in the cross-section of catheter 18 in FIG. 5, the result is a continuous and integral bond between the IV tubes 20a, b and c and the lumens 24 of catheter 18. Furthermore, this bond is continuous throughout the region B indicated in FIGS. 2 and 3. In the final configuration, the catheter 18 and the attached IV tubes 20a, b and c provide a device of unitary construction which is a structural continuum at the juncture of tube 20 and lumen 24.

Also, due to the compressive action of device 10 on catheter 18 during the welding operation, it is possible to use IV tubes 20a, b and c having thicker walls than would otherwise be possible. Indeed, in the preferred embodiment, wall thicknesses from 0.020 inches to 0.030 inches are not uncommon. Of course, walls thinner than 0.020 inches are also suitable for the present invention and walls thicker than 0.030 inches may be used depending on the compressive strength of the device 10 and the amount of RF power supplied by generator 30.

As shown in FIG. 6, in the preferred embodiment for catheter 18, IV tube 20 is formed with a chamfered tip 80 at the end of IV tube 20 that is inserted into and welded to catheter 18. The chamfered tip 80, so positioned, permits entry of a guidewire (not shown) between lumen 24 and IV tube 20 without hanging up the guidewire (not shown) at the juncture of the end of IV tube 20a with the lumen 24. As will be understood by those skilled in the art, a guidewire is often used for positioning a catheter 18 into the vein of a patient. The chamfered tip 80 also helps prevent air bubble immobilization and fluid stagnation areas at the juncture. In order to further facilitate passage of the guidewire (not shown) from lumen 24 into an IV tube 20, each lumen 24 may be preformed to establish a step 82 within the lumen 24 against which the chamfered tip 80 of IV tube 20 can be positioned. As best seen in FIG. 6, the step 82 permits an unobstructed transition for passage of the guidewire (not shown) from lumen 24 onto the chamfered surface of chamfered tip 80 and into IV tube 20. Step 82 can be preformed by inserting into a lumen 24 a mandrel (not shown) having a cross-sectional area that is substantially equivalent to the cross-sectional area of lumen 24. Sufficient RF energy from generator 30 is then supplied to the mandrel to reform lumen 24 and shape step 82.

Not shown in the drawings are the plethora of adapters and connectors which can be attached to the proximal ends of IV tubes 20a, b and c opposite from the end of their attachment with the catheter 18. As can be appreciated by those skilled in the art, such connectors can be preattached or attached as needed and can have a variety of structures dependent only on the needs of the operator. Generally, however, it is anticipated that a standard luer adapter will be most commonly incorporated.

As previously mentioned, a suitable material for the catheter 18 is a barium-filled polyurethane. In the contemplation of the present invention, IV tubes 20a, b and c are also made of a polyurethane material. The use of the same material throughout the catheter 18 and IV tube 20 combination obviates any differences in strength, durability or compatability which may occur when dissimilar materials are used. Although the expressed preference for the present invention is the use of a polyurethane material, other materials which are well known in the art and suitable for an RF welding operation may be used. In fact, dependent only on the desires of the manufacturer, the catheter 18 and IV tubes 20 may even be of dissimilar materials.

OPERATION

In the operation of the welding device 10, a mandrel 22a having electrical conductive properties, such as beryllium copper alloy, is inserted into the passageway of an IV tube 20a. The mandrel 22a and IV tube 20a combination is then inserted into a lumen 24 of a catheter 18. Likewise, mandrels 22b and c are respectively inserted into IV tubes 20b and c and these combinations are positioned into lumens 24 of catheter 18. As previously discussed the proper operation of welding device 10 is not dependent on cross-sectional conformity between the IV tube 20a, b and c and the lumens 24.

Once the combination of IV tubes 20a, b and c and mandrels 22a, b and c are inserted into lumens 24 of catheter 18, the entire combination of mandrel 22a, b and c, IV tube 20a, b and c and catheter 18 is positioned within the pathway 70 of dielectric collet 16 as shown in FIG. 1. Piston 48 is then activated to move metal collet 14 in the direction indicated by directional arrow 74 in FIG. 1. This motion causes the flanges 72 of metal collet 14 to urge against the tapered region A of adapter 12 and clampingly engage the resilient fingers 58 of metal collet 14 onto the dielectric collet 16. The urging of metal collet 14 onto dielectric collet 16 in turn causes resilient members 50 of dielectric collet 16 to clampingly engage with the catheter 18.

It should be appreciated from previous discussions that the compressive forces generated by the action of dielectric collet 16 on the catheter 18 causes the reshaping of lumens 24 and IV tubes 20 in a manner to cause a uniform and continuous contact between the outside surface of the IV tubes 20 and the side walls of lumens 24. Thus, as can be appreciated from the previous discussion, a generally circular cross-section IV tube 20 can be made to come in contact with a substantially eliptically shaped lumen 24. It should be further appreciated that the lumen 24 need not be restricted to a substantially eliptical shape. Indeed, other shapes such as semi-circles, squares or rectangles could also be used. An important feature of the present invention, as illustrated by the welding device 10 in FIG. 1, is that the compression caused by the dielectric collet 16 on the catheter 18 overcomes dimensional inconsistencies and particularly this compression overcomes dimensional inconsistencies of soft extruded materials, such as polyurethane, which are typically used in IV tubes and catheters.

With the catheter 18, IV tubes 20 and mandrels 22 positioned within the welding device 10 as shown in FIG. 1 and after welding device 10 has been operated to compress the dielectric collet 16 onto catheter 18, the exposed end of mandrel 22a opposite from the end which is associated with catheter 18 is electrically connected to a connector 26a. Connector 26a, which is in electrical contact with generator 30 through line 28, provides means for supplying RF energy from generator 30 to mandrel 22a. As previously discussed, by overcoming the dimensional inconsistencies through compression of the catheter 18 onto IV tube 20, contact between the side wall of lumen 24 and the outer surface of IV tube 20 is assured. Thus, the initial compatability or incompatability of configuration between the IV tube and the shape of lumen 24 becomes less important. A beneficial effect of this fact is that thicker walled IV tubes 20 can be welded into lumen 24 with less power required from generator 30. It is not uncommon to consider operation of the welding device 10 within a range of power supplied to mandrel 22 of from 300 to 1,000 watts.

Once the mandrels 22a, b and c, IV tubes 20a, b and c and catheter 18 combination have been placed in the welding device 10, the power supply 30 is energized and energy is passed along mandrel 22a to weld IV tube 20a to catheter 18. Sequentially, energy from generator 30 is applied to mandrels 22b and c to weld IV tubes 20b and c to catheter 18. After the welding operation is completed, the catheter 18 and IV tubes 20a, b and c are allowed to cool for a period of time. The welding device 10 is then operated to move the metal collet 14 in a direction opposite to directional arrow 74. This releases the grip or clamping effect of dielectric collet 16 on catheter 18. The catheter 18 and IV tube 20a combination can then be removed from welding device 10 and mandrels 22a, b and c can be removed from IV tubes 20a, b and c.

Catheter 18 can be dimensioned for adaptability and use as a venous catheter. When so used, the unitary construction for catheter 18, as described above, provides for multiple fluid passageways defined by the individual proximal IV tubes 20 and their associated lumens 24. As previously stated, the end of each individual IV tube 20 opposite from the catheter 18 can be specially adapted for connection with a particular fluid source (not shown). As can be appreciated by those skilled in the relevant art, the various fluid sources suitable for use with catheter 18 include IV pumps, IV controllers, IV bottles, syringes, and other specialized fluid containers. Regardless of the particular fluid source used, catheter 18 when properly positioned into the vein of a patient and the IV tubes 20 associated with catheter 18 provide an effective means for infusing medical solutions to the patient.

While the particular multilumen catheter and associated IV tubing as herein shown and disclosed in detail is fully capable of obtaining the objects and providing the advantages herein before stated, it is to be understood that it is merely illustrative of the presently preferred embodiment of the invention and that no limitations are intended to the details of construction or design herein shown other than as defined in the apended claims.

I claim:

1. A device of unitary construction for infusing medical fluids to a patient comprising:
    a catheter having a plurality of lumens of generally elliptical cross-section each lumen having a side wall inner surface surrounding the lumen;
    a plurality of tubes each with a wall defining a generally circular inside and outside cross-section and each tube separately bonded into fluid communication with a respective catheter lumen of elliptical cross-section to form a welded and reformed continuous and integral attachment along a region of an interface between the reformed outside surface of each circular cross-section tube and the side wall inner surface of the respective catheter lumen by the changed shapes of the outside surface of each tube and the maintained elliptical cross-section shape of each catheter lumen for a direct conforming fit so that a structural continuum is formed at the juncture of the tube and the catheter lumen by the changed shape of the outside surface of the tube and the maintained relative shape of the catheter lumen; and
    a chamfered tip from the circular inside cross-section of an end of each tube that is inserted into the respective catheter lumen.

2. The device of claim 1 wherein a step is provided within each catheter lumen against which the chamfered tip of the tube is positioned permitting an unobstructed transition from each catheter lumen of elliptical cross-section to the respective inside circular cross-section of each tube.

3. The device of claim 2 wherein each tube and the catheter are made of polyurethane and the welding takes place primarily along the reformed interface therebetween.

4. The device of claim 2 wherein the catheter is made of radio opaque polyurethane.

* * * * *